(12) United States Patent
Armstrong et al.

(10) Patent No.: US 6,410,828 B1
(45) Date of Patent: Jun. 25, 2002

(54) REGULATORY SEQUENCES USEFUL FOR GENE EXPRESSION IN PLANT EMBRYO TISSUE

(75) Inventors: Katherine Armstrong, Zionsville; Aaron T. Woosley, Fishers; Dayakar R. Pareddy, Carmel; Beth C. Rubin-Wilson, Indianapolis; Timothy D. Hey, Zionsville; Kelley A. Smith, Lebanon, all of IN (US); Otto Folkerts, Guilford, CT (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 09/443,732

(22) Filed: Nov. 19, 1999

Related U.S. Application Data

(60) Provisional application No. 60/109,167, filed on Nov. 20, 1998.

(51) Int. Cl.[7] .............................. A01H 1/00; A01H 5/10; C07H 21/04; C12N 5/14; C12N 15/82
(52) U.S. Cl. .................... 800/287; 435/320.1; 435/419; 435/468; 536/24.1; 800/298
(58) Field of Search .............................. 435/320.1, 468, 435/419; 536/23.1, 24.1; 800/278, 287, 298

(56) References Cited

PUBLICATIONS

Benfey et al. The Cauliflower Mosaic Virus 35S promoter: combinatorial regulation of transcription in plants. Science, vol. 250, pp. 959–966, especially pp. 960, 963, 1990.*

Kim et al. A 20 nucleotide upstream element is essential for the nopaline synthase (nos) promoter activity. Plant Molecular Biology vol. 24, pp. 105–117, especially p. 109, 1994.*

\* cited by examiner

*Primary Examiner*—Elizabeth F. McElwain
*Assistant Examiner*—Cynthia Collins
(74) *Attorney, Agent, or Firm*—Donald R. Stuart

(57) ABSTRACT

This invention relates to compositions and methods useful in the production of transgenic plants. In particular, the invention relates to maize metallothionein gene transcription regulatory sequences which are useful for directing expression of heterologous DNAs in plant embryo tissue. The invention also relates to expression cassettes containing the promoter sequences and to transgenic plants containing the expression cassettes.

5 Claims, No Drawings

REGULATORY SEQUENCES USEFUL FOR GENE EXPRESSION IN PLANT EMBRYO TISSUE

RELATED APPLICATIONS

This application claims priority from U.S. Provisional Patent Application Ser. No. 60/109167, filed Nov. 20, 1998.

BACKGROUND OF THE INVENTION

The present invention relates to plant molecular biology. In particular, it relates to promoter sequences useful for gene expression in selected plant organs and tissues.

Isolated plant promoters are useful in the genetic engineering of plants to produce transgenic plants with desired phenotypes. To produce such transgenic plants, an isolated plant promoter is inserted into a vector and operably linked to a heterologous DNA sequence. Plant cells are then transformed with the vector such that expression of the heterologous DNA is controlled by the promoter.

Some plant promoters are tissue-specific, while others are constitutive and drive expression in essentially all tissues and organs. Tissue-specific promoters can be identified from genes that are expressed in particular tissues or at particular times during development.

A need exists for a variety of different promoters to be used in the genetic engineering of plants. New tissue-specific promoters are particularly useful for the controlled expression of various nucleic acid sequences in transgenic plants. The present invention addresses these and other needs.

SUMMARY OF THE INVENTION

The present invention provides embryo specific maize metallothionein promoters. The promoters can be used to provide embryo specific expression of the heterologous sequences in plants. In particular, the promoters are useful in expression in maize. More specifically, the invention provides an isolated DNA molecule comprising base pairs 50 to 1649 of SEQ ID NO:5, or a fragment, genetic variant or deletion of such a sequence which retains the ability of functioning as an embryo specific promoter in plant cells.

The invention also provides expression cassettes comprising an embryo specific promoter operably linked to a heterologous nucleic acid sequence, wherein the promoter selectively hybridizes to a 20 consecutive base pair portion of the sequence set forth in SEQ ID NO:5.

The invention also provides an expression cassette of wherein the promoter comprises a sequence extending from about nucleotide 50 to nucleotide 1649 of SEQ ID NO:5.

The invention also provides a method of expressing a heterologous nucleic acid sequence in a plant comprising:

a) introducing into plant tissue a vector comprising an embryo specific maize metallothionein promoter operably linked to the heterologous nucleic acid sequence; and b) regenerating the plant tissue into a whole plant.

The invention also provides an isolated DNA molecule having a 20 base pair nucleotide portion identical in sequence to a 20 consecutive base pair portion of the sequence set forth in SEQ ID NO:5.

The invention also provides transgenic plant comprising the expression cassettes described above. The plant may be any agronomically useful plant.

DEFINITIONS

The term "nucleic acids", as used herein, refers to either DNA or RNA. "Nucleic acid sequence" or "polynucleotide sequence" refers to a single- or double-stranded polymer of deoxyribonucleotide or ribonucleotide bases read from the 5' to the 3' end. Sequence regions on a DNA strand that are 5' to the 5' end of an RNA transcript encoded by the DNA are referred to as "upstream sequences". Upstream sequences are usually counted in a negative direction from the transcription start site. Sequence regions on the DNA strand that are 3' to the 3' end of the RNA transcript are referred to as "downstream sequences."

The term "promoter" refers to a region of DNA upstream from the translational start codon and which is involved in recognition and binding of RNA polymerase and other proteins to initiate transcription. A "plant promoter" is a promoter capable of initiating transcription in plant cells. The term maize metallothionein promoter as used herein refers to plant promoters comprising sequences derived from the promoter region of a maize metallothlonein gene. The promoters of the invention contain tissue specific elements that allow embryo specific transcription of operably linked DNA sequences. The promoters are considered to be embryo specific promoters because transcription of the operably linked DNA is higher in embryo tissues than it is in other tissues.

A "tissue-specific" promoter as used herein refers to a promoter that drives expression of an operably linked nucleic acid sequence in a particular tissue in a plant or at a particular stage in the plant life-cycle.

The term "operably linked" as used herein refers to linkage of a promoter upstream from a DNA sequence such that the promoter mediates transcription of the DNA sequence. It is understood that the promoter sequence aim includes transcribed sequences between the transcriptional start and the translational start and the translational start codon.

The phrase "expression cassette", refers to nucleotide sequences which are capable of affecting expression of a structural gene in hosts compatible wanh such sequences. Such cassettes include at least promoters and optionally, transcription termination signals. Additional factors necessary or helpful in effecting expression may also be used as described herein.

A "heterologous" nucleic acid or protein is one that originates from a foreign source (or species) or, if from the same source is modified from its original form. Thus, a heterologous promoter sequence in an expression cassette is from a source different from the source of the coding sequence, or, if from the same source, is modified from its original form. Modification may occur, e.g., by treating the DNA with a restriction enzyme to generate a promoter element that is capable of conferring tissue-specific expression on the expression cassette which includes it.

The phrases "isolated" or "substantially pure" when referring to a polynucleotide or protein, means a chemical composition which is free of other subcellular components of the organism from which it its derived. Typically, a compound is substantially pure when at least about 85% or more of a sample exhibits a single polypeptide backbone, or polynucleotide sequence. Minor variants or chemical modifications may typically share the same polypeptide sequence. Depending on the purification procedure, purity of 85%, and preferably over 95% pure are possible. Nucleic acid and protein purity or homogeneity may be indicated by a number of means well known in the art, such as gel electrophoresis and the like.

The term "plant" includes whole plants, plant organs (e.g., leaves, stems roots, etc.), seeds and plant cells and progeny of same. The class of plants which can be used in the method of the invention is generally as broad as the class of higher plants amenable to transformation techniques, including both monocotyledonous and dicotyledonous plants.

"Percentage of sequence identity" for polynucleotides and polypeptides is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by computerized implementations of known algorithms (e.g., GAP, BESTFIT, PASTA, and TFASTA in the Wisconsin Genetics Software Package, Genetics Computer Group (GCG), 575 Science Dr., Madison, Wis., or BlastN and BlastX available from the National Center for Biotechnology Information), or by inspection. Sequences are typically compared using GESTFIT or BlastN with default parameters.

Substantial identity of polynucleotide sequences means that a polynucleotide comprises a sequence that has at least 75% sequence identity, preferably at least 80%, more preferably at least 90% and most preferably at least 95%. Typically, two polypeptides are considered to be substantially identical if at least 40%, preferably at least 60%, more preferably at least 90%, and most preferably at least 95% are identical or conservative substitutions. Polypeptides which are "substantially similar" share sequences as noted above except that residue positions which are not identical may differ by conservative amino acid changes. Conservative amino acid substitutions refer to the interchangeability of residues having simnilar side chains.

Another indication that polynucleotide sequences are substantially identical is if two molecules selectively hybridize to each other under stringent conditions. The phrase "selectively hybridizing to" refers to a nucleic acid probe that hybridizes or binds only to a particular target DNA or RNA sequence when the target sequences are present in a preparation of total cellular DNA or RNA. Stringent conditions are sequence dependent and will be different in different circumstances. Generally, stringent conditions are selected to be about 20° C. lower than the thermal melting point (Tm) for the specific sequence at a define ionic strength and pH. The Tm is the temperature (under defined ionic strength and pH) at which 50% of the target sequence hybridizes to a perfectly matched probe.

BRIEF DESCRIPTION OF THE SEQUENCES

SEQ ID NO:1 is the DNA sequence of the SK primer.

SEQ ID NO:2 is cDNA sequence for Maize Ec Metallothionein

SEQ ID NO:3 is the DNA sequence for clone 651, containing the first 233 bases of the coding region for Maize Ec Metallothionein.

SEQ ID NO:4 is the DNA sequence for the T3 primer.

SEQ ID NO:5 is the DNA sequence for clone MGN 111-1.

DETAILED DESCRIPTION

The present invention provides new plant promoter sequences useful for expression of desired nucleic acid sequences in plant embryos. In particular, the invention provides isolated nucleic acid molecules comprising sequences from promoters derived from a maize metallothionein gene. The promoter sequences of the invention can be used to drive expression of a variety of heterologous nucleic acids sequences in embryo tissue of transgenic plants.

I. Isolation of Maize Metallothionein Promoters

The promoter sequences of the invention are typically identical to or show substantial sequence identity (determined as described above) to portions of the maize metallothionein promoter nucleotide sequence depicted in bp 50-1649 of SEQ ID NO: 5. A number of different promoters having homology or substantial sequence identity to the promoter sequences of SEQ ID NO:5 can be isolated from maize.

Maize metallothionein promoter sequences typically hybridize to a nucleic acid having a sequence as shown in bp 50-1649 of SEQ ID NO: 5 under stringent conditions. Typically stringent conditions for a Southern blot protocol involve washing at 55° C. with 0.2×SSC.

There are a variety of methods that may be used for isolation of maize metallothionein promoter sequences. For example, DNA can be isolated from a genomic library using labeled nucleic acid probes having sequences complementary to the sequences disclosed here. Full-length probes may be used, or oligonucleotide probes may also be generated. Alternatively, genomic clones comprising the genes can be isolated and the 5' end of the clones can be subcloned to provide the promoter sequences. Techniques for nucleic acid manipulation of genes such as subcloning nucleic acid sequences encoding polypeptides into expression vectors, labeling probes, DNA hybridization, and the like are described generally in Sambrook, et al., *Molecular Cloning—A Laboratory Manual* (2nd Ed.), Vol. 103, Cold Spring Harbor Laboratory, Cold Spring Harbor, N.Y. (1989). This manual is hereinafter referred to as "Sambrook, et al."

In addition to screening using the sequences disclosed here, techniques designed to identify sequences specific to a particular tissue or cell types can be used to isolate sequences of the invention (see, e.g., Sambrook, et al.) Such techniques include differential hybridization techniques as described in the example section or in Gurr, et al. *Mol. Gen. Genet.* 226:361–366 (1991). In addition, subtractive hybridization techniques can be used to prepare specific probes for screening cbNA or genomic libraries. These techniques can also be used to prepare subtracted libraries enriched for the desired sequences. Once a desired genomic clone is identified, the 5' sequences can be analyzed to identify the promoter sequence from the gene. This can be accomplished by inserting 5' sequences in front of a promoterless reporter gene (e.g., GUS) to identify those regions which can drive expression of a structural gene.

Nucleic acid amplification techniques such as polymerase chain reaction (PCR) technology, can also be used to amplify the desired genes and promoter sequences from mRNA, from cDNA, and from genomic libraries or cDNA libraries. In PCR techniques, oligonucleotide primers based on the sequences disclosed here and complementary to the two 5' and 3' borders of the DNA region to be amplified are synthesized. The polymerase chain reaction is then carried out using the two primers. See PCR Protocols: *A Guide to Methods and Applications* (Innis, M, Gelfand, D., Sncnsky, J. and White, T., eds.), Academic Press, San Diego (1990). Primer s can be selected to amplify the entire regions encoding a full-length isocitrate lyase or its promoter. PCR can also be used to amplify smaller DNA segments of these regions as desired.

Oligonucleotides for use as primer or probes in the above-mentioned procedures can be chemically synthesized according to standard techniques such as the solid phase phosphoramidite triester method first described by Beaucage, et al. *Tetrahedron Lett.* 22(20): 1859–1862 (1981), using an automated synthesizer, as described in Needham-Van Devanter, et al., *Nucleic Acids Res.* 12:6159–6168 (1984).

Typically, the maize metallothionein promoters of the invention will be about 170 nucleotides to about 1800 nucleotides in length, usually between about 200 to about 1500 nucleotides.

As demonstrated below, sequences which confer tissue specific expression are found in the promoters of the invention. Thus, heterologous promoters can be constructed which have tissue specific expression as a result of the presence of tissue specific elements contained in these sequences.

An additional important element is the 5' untranslated leader, i.e. the 5' end of the mRNA extending from the 5' CAP site to the AUG translation initiation codon of the mRNA. The leader plays a critical role in translation initiation and in regulation of gene expression. For most eukaryotic mRNAs, translation initiates with the binding of the CAP binding protein to the mRNA CAP. This is then followed by the binding of several other translation factors, as well as the 43S ribosome pre-initiation complex. This complex travels down the mRNA molecule while scanning for an AUG initiation codon in an appropriate sequence context. Once this has been found, and with the addition of the 60S ribosomal subunit, the complete 80S initiation complex initiates protein translation. Pain (1986); Moldave (1985); Kozak (1986). Optimization of the leader sequence for binding to the ribosome complex has been shown to increase gene expression as a direct result of improved translation initiation efficiency. Significant increases in gene expression have been produced by addition of leader sequences from plant viruses or heat shock genes. Raju et al. (1993); (Austin, 1994). Dietrich et al. (1987) reported that the length of the 5' non-translated leader was important for gene expression in protoplasts.

Specific embodiments of the invention include the following portions of SEQ ID NO:5:

| bp of SEQ ID NO:5 | description |
| --- | --- |
| 50–1649 | long promoter + untranslated leader |
| 916–1649 | promoter + untranslated leader |
| 1383–1649 | critical sequence for embryo specific expression and untranslated leader |
| 1466–1649 | minimal promoter and untranslated leader |
| 50–1557 | long promoter |
| 916–1557 | promoter |
| 1383–1557 | critical sequences for embryo specific expression |
| 1466–1557 | minimal promoter |
| 1383–1465 | critical sequences for embryo specific expression |
| 1558–1649 | untranslated leader sequence |

II. Construction of Expression Cassettes and Vectors

The methods required for construction of vectors containing expression cassettes comprising a promoter of the invention operably linked to desired sequence are well known. The minimal requirements of the vector are that the desired nucleic acid sequence be introduced in a relatively intact state. Thus, any vector which will produce a plant carrying the introduced DNA sequence should be sufficient. The selection of vectors and methods to construct them are commonly known to persons of ordinary skill in the art and are described in general technical references (See, in general, *Methods in Enzymology* Vol. 153 ("Recombinant DNA Part D") 1987, Wu and Grossman Eds., Academic Press.

The recombinant vectors of the present invention typically comprise an expression cassette designed for initiating transcription of the desired polynucleotide sequences in plants. Companion sequences, of bacterial origin, are also included to allow the vector to be cloned in a bacterial host. The vector will preferably contain, a broad host range prokaryote origin of replication. A selectable marker should also be included to allow selection of bacterial cells bearing the desired construct. Suitable prokaryotic selectable markers include resistance to antibiotics such as kanamycin or tetracycline.

For expression of polypeptides in plants, the recombinant expression cassette will contain, in addition to the desired polynucleotide sequence and the promoter sequence of the invention, a translation initiation site (if the sequence to be transcribed lacks one), and a transcription termination sequence. Unique restriction enzyme sites at the 5' and 3' ends of the cassette are typically included to allow for easy insertion into preexisting vector.

In the construction of heterologous promoter/structural gene combinations, the promoter is preferably postponed about the same distance from the heterologous transcription start site as it is from the transcription start site in the natural setting. As is known in the art, however, some variations in this can be accommodated without loss of promoter function.

As noted above, an expression cassette should also contain a transcription termination region downstream of the structural gene to provide for efficient termination. The termination region may be obtained from the same gene as the promoter sequence or may be obtained from different genes.

If the mRNA encoded by the structural gene is to be efficiently translated, polyadenylation sequences are also commonly added to the vector construct. Alber and Kawasaki, *Mo. and Appl. Genet,* 1:419–434, 1982, Polyadenylation sequences include, but are not limited to the Agrobacterium octopine synthase signal (Gielen et al., *EMBO J.,* 3:835–846, 1984) or the nopaline synthase signal (Depicker et al.) *Mol. and Appi. Genet,* 1:561–573,1982).

The vector will also typically contain a selectable marker gene by which transformed plant cells can be identified in culture. Usually, the marker gene will encode antibiotic or herbicide resistance. These markers include resistance to G418, hygromycin, bleomycin, kanamycin, gentamicin, Basta™, and chlorsulfuron. After transforming the plant cells, those cells having the vector will be identified by their ability to grow in a medium containing the particular antibiotic.

Examples of suitable structural genes that can be expressed using the promoter sequences of the invention include genes for herbicide resistance; genes for fungal disease resistance (e.g., chitinases and glucanases); genes for bacterial disease resistance (e.g., cecropins); genes for insect resistance (e.g., *B thuringiensis* toxin); and genes which modify the oil or amino acid contents of the embryo.

III. Production of Transgenic Plants

Techniques for transforming a wide variety of higher plant species are well known and described in the literature. See, for example, Weising, et al., *Ann. Rev. Genet.* 22:421–477 (1988). DNA constructs containing the promoter sequenced linked to heterologous DNA can be introduced into genome of the desired plant host by a variety of conventional techniques. For example, the DNA construct may be introduced directly into the genomic DNA of the plant cell using techniques such as electroporation and microinjection of plant cell protoplasts. Alternatively, the DNA constructs can be introduced directly to plant tissue using ballistic methods, such as DNA particle bombardment. Usually, the DNA constructs are combined with suitable T-DNA flanking regions and introduced into a conventional *Agrobacterium tumefaciens* host vector.

Direct transformation techniques are known in the art and well described in the scientific literature. The introduction of DNA constructs using polyethylene glycol precipitation is described in Paszkowski, et al., *Embo J.* 3:2717–2722 (1984). Electroporation techniques are described in Fromm, et al., *Proc. Natl. Acad. Sci. USA* 82:5824 (1985). Ballistic transformation techniques are described in Klein, et al., *Nature* 327:70–73 (1987). Whisker-mediated transformation is described in Frame et al., *Plant J.* 6:941–948 (1994).

Agrobacterium-mediated transformation techniques are the most commonly used techniques and are well described in the scientific literature. See, for example Horsch, et al *Science* 233:496498 (1984), and Fraley, et al., *Proc. Natl. Acad. Sci. USA* 80:4803 (1983).

The expression of the heterologous DNA sequences can be detected in a variety of ways, depending on the nature of heterologous sequences. For instance, resistance to an herbicide or pathogen can be detected by treatment with the herbicide or pathogen. Expression can be detected by measurement of the specific RNA transcription product. This can be done by, for example, Northern blot procedures. If heterologous DNA sequences encode a novel protein, the protein product may be assayed, for instance, by its function or by a variety of immunoassay techniques.

Transformed plant cells which are derived by any of the above transformation techniques can be cultured to regenerate a whole plant which possesses for desired. transformed phenotype. Plant regeneration from cultured protoplasts is described in Evans, et al., *Protoplast Isolation and Culture, Handbook of Plant Cell Culture,* MacMillan Publishing Company, New York, pp. 124–176 (1983); and Binding, *Regeneration of Plants, Plant Protoplasts,* CRC Press, Boca Raton, pp. 21–73 (1985). Regeneration can also be obtained from plant callus, explants, organs, or part thereof. Such regeneration techniques are described generally in Klee, et al., *Ann Rev. of Plant Phys.* 38:467–486 (1987)1

One of skill will recognize that, after an expression cassette comprising a maize metallothionein promoter sequence is stably incorporated in transgenic plants and confirmed to be operable, it can be introduced into other plants by sexual crossing. Any of a number of standard breeding techniques can be used, depending upon the species to be crossed.

The promoter sequences of the invention can be used in the transformation of any plant, including both dicots and monocots. Transformation of dicots is described in references above. Transformation of monocots is known using various techniques including electroporation (e.g., Shimamoto, et al., *Nature* 338:274–476 (1992); ballistics (e.g., European Patent Application 270,356); and Agrobacterium (e.g., Bytebier, et al., *Proc. Natl. Acad. Sci USA* 84:5345–5349 (1987).

The methods and compositions of the invention have use over a broad range of types of plants.

IV. EXAMPLES

The following examples are provided by way of illustration and not limitation.

Example 1

Sequencing And Analysis Of cDNAs

Maize embryo-specific cDNAs were identified by randomly sequencing individual clones from a maize embryo cDNA library.

A. Preparation of the Maize Embryo cDNA Library

The cDNA library was prepared from kernels harvested at 20 DAP (days after pollination) from maize inbred line CS608 that had been grown in the greenhouse. Embryos from the kernels were collected, immediately frozen on dry ice, and stored at −70° C. RNA was extracted by grinding the embryos (2.5 g.) to a fine powder in liquid nitrogen. Ten mL of extraction buffer [50 mM Tris-HCl, pH 8.0, 4% para-amino salicylic acid (Sigma Chemical Co., St. Louis, Mo.), 1% tri-iso-propylnaphtalenesulfonic acid (Eastman Kodak Co., Rochester, N.Y.), 10 mM dithiothreitol (DTT) (Bethesda Research Labs, Gaithersburg, Md.) and 10 mM sodium meta-bisulfite (Sigma Chemical Co.)] were then added and the mixture was homogenized for 1 min using a TEKMAR TISSUMIZER (Tekmar Co., Cincinnati, Ohio). The homogenate was extracted with an equal volume of phenol equilibrated with 0.1 M Tris-HCl, pH 8.0. Organic and aqueous phases were separated by centrifugation at 40° C. The aqueous phase was removed and extracted with an equal volume of chloroform/octanol (24:1). The supernatant was then transferred, centrifuged, transferred again and a one-half volume of 7.5 M ammonium acetate (pH 8.0) was added. RNA was then precipitated on ice for 30 min.

Precipitated RNA was collected by centrifugation and dissolved in 1 mL of DEPC-water (diethylpyrocarbonate-treated water) (0.1% v/v). One-half volume of 7.5 M ammonium acetate (pH 8.0) and two volumes of 100% ethanol were added followed by RNA precipitation at −20° C. for 30 min. The precipitate was collected by centrifugation, washed in ice-cold 70% ethanol, air dried, and dissolved in 0.5 mL DEPC-treated water.

PolyA+ mRNA was purified on oligo dT-cellulose (Collaborative Biomedical Products, Bedford, Mass.) columns. Type 3 oligo-dT cellulose (0.1 g) was equilibrated in 5 mL of buffer 1 for 30 min, wherein buffer 1 is loading buffer with 0.5 M NaCl and loading buffer is 20 mM Tris-HCl, pH 7.6, 1 mM ethylenediaminetetraacetic acid (EDTA), and 0.1% sodium lauryl sulfate (SDS). The poured column was washed with 3 volumes of DEPC-water, 3 volumes of wash buffer [0.1 N NaOH, 5 mM EDTA], 3 volumes of DEPC-water, and 5 volumes of buffer 1. The dissolved RNA pellet was heated at 65° C. for 5 min, diluted 2× with buffer 2 [2× loading buffer] and then applied to the oligo-dT column. The flow through material was collected, reheated, and reapplied to the column. The column was then washed with 10 volumes of buffer 1 followed by 10 volumes of buffer 3 [loading buffer having 0.1 M NaCl]. PolyA$^+$ RNA was eluted with 3 volumes of elution buffer [10 mM Tris-HCl, pH 7.5, 1 mM EDTA, 0.05% SDS] and collected in 0.5 mL fractions. RNA fractions were combined, buffered to 0.3 M sodium acetate pH 5.2, and precipitated at −20° C. for 16 h after addition of 2.2 volumes of 100% ethanol. The precipitate was collected by centrifugation, washed with 70% ethanol, dried, and dissolved in 50 $\mu$L DEPC-treated water. This material was then repurified on a fresh oligo-dT column, as described above, to produce highly-enriched polyA$^+$ mRNA. RNA concentrations were determined by measuring $OD_{260\ nm}$.

Five $\mu$g of polyA$^+$ RNA was converted to cDNA and cloned into the LAMBDA UNI-ZAP vector using the Lambda ZAP-cDNA synthesis and cloning kit according to the manufacturers protocols (Stratagene, La Jolla, Calif.).

The resulting library had an original titer of 3.38×10¹⁰ plaque forming units/mL (pfu/mL), greater than 95% recombinants and an average insert size of 1.35 kb. The cDNA library was amplified according to Sambrook et al., (Molecular Cloning, A Laboratory Manual, $2^{nd}$ Ed. (1989) Cold Spring Harbor Laboratory Press) and had a titer of 6.0×10⁶ pfu/mL. Total library cDNA was batch rescued and isolated as follows: 5 mL of XL1 Blue *E. coli* cells (Stratagene) at $OD_{600nm}$ =1.0 in 10 mM $MgSO_4$ were mixed with 8.3 μL (5×10⁸ pfu) of amplified embryo cDNA library phage-stock, and 100 μL EXASSIST helper phage (Stratagene) and incubated at 37° C. for 20 min. Twenty-five mL of TY medium, pH 7.8 [8.0 g/L tryptone, 5.0 g/L yeast extract, and 2.5 g/L NaCl] was added and cells were incubated at 37° C. for 3 h while shaking. Afterwards, the bacterial cells were heat killed at 68° C. for 15 min and the supernatant was recovered. Five hundred μL supernatant was mixed with 14.5 mL of SOLR cells (Stratagene) ($OD_{600\ nm}$ =1.5), incubated at 37° C. for 15 min, added to 500 mL LB [10 g/L tryptone, 10 g/L NaCl, and 5 g/L yeast extract containing Ampicillin (50 μg/mL), and grown overnight. Afterwards, plasmid DNA was obtained by alkaline lysis/CsCl purification, according to Sambrook et al (Molecular Cloning, A Laboratory Manual, $2^{nd}$ Ed. (1989) Cold Spring Harbor Laboratory Press) and analyzed by agarose gel electrophoresis following digestion with EcoR/XhoI. A smear ranging from 0.5 to 3.0 kb was observed following electrophoresis.

B. Rescue of phagemid, DNA extraction and Sequencing:

Phage were plated out as described in the protocols provided with the ZAP-cDNA® Synthesis Kit (Stratagene, La Jolla, Calif.) to achieve a density of 100 pfu per 110 mm petri plate. Individual plaques were cored out and stored in 500 mL SM Buffer (per liter: 5.8 g NaCl, 2.0 g $MgSO_4$, 50 mL 1 M Tris-Cl, pH 7.5, 5 mL 2% gelatin) and allowed to diffuse for 1–2 hours at room temperature or overnight at 4° C. Phage were rescued into phagemid form by in vivo excision and recircularization using protocols described by Stratagene, with the following modifications. To a 5 mL sterile FALCON 2059 tube the following components were added: 200 mL of XL1-BLUE cells (Stratagene) grown to an OD600 of 1.0; 100 mL of phage stock in SM; 1 mL EXASSIST (Stratagene) helper phage. This mixture was incubated at 37° C. for 15 minutes. Three mL of 2× YT broth (per liter: 10 g NaCl, 10 g yeast extract, 16 g tryptone) were added to the tubes which were then incubated at 37° C. for 2–2.5 hours with shaking. Tubes were heated at 65° C.–70° C. for 20 minutes, and then 1 mL aliquots were transferred to sterile microfuge tubes which were spun for 5 minutes at 12,000×g. This supernatant contains the plasmid packaged as a filamentous phage particle. Rescued phagemid were plated by combining 200 mL SOLR cells (Stratagene) grown to OD600=1.0 with 1 mL phage stock described above. Tubes were incubated at 37° C. for 15 minutes. Cells containing rescued phagemid were streaked onto LB agar plates (per liter: 10 g NaCl, 10 g Bacto-tryptone, 5 g yeast extract, 15 g agar) containing 75 mg/mL ampicillin, and grown overnight at 37° C. Single colonies were grown up in 3 mL LB broth for phagmid DNA extraction using QIAWELL Plasmid Purification System (Qiagen, Santa Clarita, Calif.).

C. Sequencing and Analysis

Plasmid DNA was sequenced using the PRISM Ready Reaction DYEDEOXY Terminator Cycle Sequencing Kit (Perkin Elmer/Applied Biosystems Divison, Foster City, Calif.) according to protocol #401388. The primer used for sequencing the 5' end of the cDNAs corresponds to the SK primer (Stratagene) and is given herein as SEQ ID NO:1: 5' CGC TCT AGA ACT AGT GGA TC 3'. 5' end single pass sequences were obtained using a ABI PRISM 373 DNA Sequencer (Perkin Elmer/Applied Biosystems Division). Sequencing reactions were edited for ambiguities using SEQED 675 DNA Sequence Editor (Perkin Elmer/Applied Biosystems Division) software. Sequences containing fewer than 10 ambiguous base calls in 300 bases were submitted for database searching using the Wisconsin Sequence Analysis Package (Genetics Computer Group, Madison, Wis.) FastA program. Ten clones out of 390 randomly sequenced clones from the maize embryo cDNA library had between 96% and 99% identity with GenBank accession #U10696 which encodes a putative maize Ec metallothionein homologue (unpublished, Carol J. Rivin, Botany and Plant Pathology, Oregon State University, Corvallis, Oreg.). Plasmid p8.5Ec was selected for sequencing of the entire cDNA. The cDNA sequence encoding maize Ec metallothionein is given in the Sequence Listing as SEQ ID NO: 2.

D. Description of plasmid p8.5Ec

Plasmid p8.5Ec is a 3502 bp plasmid containing the maize Ec metallothionein cDNA cloned into the EcoR1 and Xho I restriction sites of pBluescript® SK+ (Stratagene®, La Jolla, Calif.). The DNA sequence of p8.5Ec is based upon the following sequence assignments: nucleotide 1 corresponds to the A of the ATG codon which encodes the methionine of the ampicillin resistance gene and proceeds on the sense DNA strand toward the stop codon of the ampicillin resistance gene, and then toward the ATG of the lacZ gene. Nucleotides 1-2127 of p8.5Ec are the reverse complement of nucleotides 707-2833 of the pBluescrlpt® SK+ plasmid as provided on the Stratagene® internet web site; bases 2128-2133 are the unique EcoR1 cloning site GAATTC; bases 2134-2139 are GGCACG; bases 2140-2704 correspond to the metallothlonein 8.5 cDNA (SEQ ID NO:2); bases 2705-2710 are the unique Xho I cloning site; bases 2711-3502 correspond to the reverse complement of nucleotides 1-667/2834-2958 of the pBluescript®SK+ plasmid as described on the Stratagene® internet web site.

Example 2

Analysis of Tissue Specific Expression and Developmental Patterns in Seed

Dow AgroSciences proprietary maize genotypes CS608, HO1, CQ806, OQ414, and HiII, and a commonly available inbred B73, were grown under standard greenhouse conditions. For analysis of tissue specific gene expression of the metallothionein gene (Met), tissues were harvested at the developmental times of interest and frozen at −70° C. until RNA extraction. The following tissues and genotypes were analyzed: Lane 1. HiII callus, 2. Roots of genotype B73 at 23 days after germination, 3. B73 roots at 63 d., 4. B73 leaf at 23 d., 5. HiII leaf at 60d. 6. Tassel of genotype B73 at emergence, 7. B73 silk at emergence, 8. B73 kernel at 20 days after pollination (DAP), 9. B73 endosperm at 20 DAP 10. CS608 embryo at 20 DAP, 11. HO1 embryo at 20 DAP, 12. CQ806 embryo at 20 DAP, 13. OQ414 embryo at 20 DAP, 14. HiII embryo at 20 DAP.

For determination of the temporal expression pattern of Met in seed embryos, kernels were dissected from ears of CQ806 and HO1 at different days after pollination (DAP). The following genotypes and developmental stages were analyzed: Lanes 1–7 CQ806 embryos at 15, 18, 21, 24, 27, 30, and 34 DAP respectively, lanes 8–14 HO1 embryos at 13, 15, 19, 23, 25, 29, and 31 DAP respectively.

Kernels were dissected immediately after they were harvested, and embryos were collected and frozen in 50 mL conical tubes on dry ice. Frozen material was stored at −70°

C. until RNA extraction. RNA was extracted by grinding the tissues or embryos (2.5 g) to a fine powder in liquid nitrogen. Ten mL of extraction buffer [50 mM Tris-HCl, pH 8.0, 4% para-amino salicylic acid (Sigma Chemical Co., St.

Louis, Mo.), 1% tri-iso-propylnaphtalenesulfonic acid (Eastman Kodak Co., Rochester, N.Y.), 10 mM dithiothreitol (DTT) (Bethesda Research Labs, Gaithersburg, Md.) and 10 mM sodium meta-bisulfite (Sigma Chemical Co.)] was then added and the mixture was homogenized for 1 min using a TEKMAR TISSUMIZER (Tekmar Co., Cincinnati, Ohio). The homogenate was extracted with an equal volume of phenol equilibrated with 0.1 M Tris-HCl, pH 8.0. Organic and aqueous phases were separated by centrifugation at 4° C. The acueous phase was removed and extracted with an equal volume of chloroform/octanol (24:1). The supernatant was then transferred, centrifuged, transferred again and a one-half volume of 7.5 M ammonium acetate (pH 8.0) was added. RNA was then precipitated on ice for 30 min. Precipitated RNA was collected by centrifugation and dissolved in 1 mL of diethylpyrocarbonate-treated water (0.1% v/v), hereinafter DEPC-water. One-half volume of 7.5 M ammonium acetate (pH 8.0) and two volumes of 100% ethanol were added followed by RNA precipitation at −20° C. for 30 min. The precipitate was collected by centrifugation, washed in ice-cold 70% ethanol, air dried, and dissolved in 0.5 mL DEPC-treated water. For expression analysis 2 μg RNA per sample was fractionated by electrophoresis in non-denaturing 10 mM $NaPO_4$ pH 6.8, 1.0% agarose gels. The volume of sample containing 2 μg of RNA was diluted to 8 μL with DEPC-water, and denatured with an equal volume of 2× sample buffer [40 mM $NaHPO_4$ pH6.8, 10 mM EDTA, 6% formaldehyde, 50% formamide] and heated to 68° C. for 15 min. The denatured sample was chilled on ice and 4 μL loading buffer [50% glycerol, 10 mM EDTA, 5 mM $NaPO_4$, pH 6.8, 0.25% bromophenol blue] was added. The samples were loaded on the gel and electrophoresed for 3 h at 60 V in 10 mM phosphate buffer. RNA was transferred from the gel to GENESCREEN PLUS membrane (NEN Research Products) by capillary transfer with sterile water as the transfer medium. Following transfer the RNA was cross-linked to the membrane using a UV STRATALINKER (Stratagene). The RNA blot was prehybridized for 3 h at 42° C. in hybridization buffer [50 mM sodium phosphate pH6.5, 0.8 M NaCl, 1 mM EDTA, 0.2% SDS, 0.05% bovine serum albumin, 0.05% Ficoll Type40, 10% dextran sulfate]. A hybridization probe specific for the Met coding region was obtained by digestion of plasmid p8.5EcMet with the enzymes EcoR1 and Xho1, followed by gel purification gel of the 550 bp Met fragment. Twenty nanogram of gel-purified fragment was labeled with 50 μCi [α-32P]-dCTP (NEN Research Products) using READY-TO-GO labeling beads (Pharmacia) according to the manufacturer and purified over NUCTRAP push columns (Stratagene). The labeled probe was denatured by boiling for 5 min, chilled on ice for 5 min, and added directly to the prehybridized blots. Hybridization was done in SEAL-A-MEAL bags (DAZEY Corp., Industrial Airport, Kans.), at 42° C. for 16 h. Blots were washed six times for 30 min in large excess (500 mL) of pre-warmed washing solution [20 mM sodium phosphate pH6.5, 50 mM NaCl, 1 mM EDTA, and 0.1% SDS] at 60° C. The blots were exposed to Kodak X-OMAT film (Eastman Kodak Co., Rochester, N.Y.) using an intensifying screen (DuPont Cronex) at −70° C. The results demonstrated that the Met gene is expressed in an embryo specific manner.

Example 3

Cloning of the Promoter from the Embryo Specific Maize Metallothionein Gene

A maize (inbred OQ414) genomic library was constructed by Stratagene Cloning Systems (La Jolla, Calif.) using genomic DNA which was purified at Dow AgroSciences using standard CTAB extraction protocols. The library was constructed using Lambda DASH™ II Vector (Stratagene Cloning Systems, La Jolla, Calif.). The library was grown in Epicurian Coli® XL1-Blue MR cells as suggested by the manufacturer (Stratagene Cloning Systems, La Jolla, Calif.). A total of $2 \times 10^6$ plaques were screened using a 700 basepair EcoRI/XhoI cDNA fragment from clone 8.5 as a template for probe synthesis with a random labeling kit (Boehringer-Mannheim, Indianapolis, Ind.). Three positive clones (λ Met2, λ Met12 and λ Met14) were identified after repeated rounds of plaque hybridization. DNAs purified from these clones were restricted with several enzymes and characterized by Southern blot analysis. Restriction mapping indicated that the phage insert contained only the 5' end of the coding sequence, but at least 15 kilobases of 5' untranslated sequences which would contain the promoter sequence. All three phage had the identical restriction patterns with a 16 kilobase insert. One clone, λ Met14, was chosen for further analysis. An 1800 base pair EcoRI fragment which hybridized to the cDNA probe was excised from a 1.0% agarose gel and the DNA was purified using Qiaex II (Qiagen, Hilden, Germany) and ligated into the EcoRI cloning site of pBluescript®II SK(−) (Stratagene, Inc.). (Restriction endonucleases and T4 DNA ligase was obtained from Bethesda Research Laboratories (Bethesda, Md.) Ligations were transformed into DH5((Laboratory, Bethesda, Md.). Recombinant plasmids were selected on Luria agar (Gibco, Bethesda, Md.) containing 75 mg/liter ampicillin (Sigma, St. Louis, Mo.) and 40 mL/plate of a 40 mg/mL stock of X-gal (Boehringer Mannheim, Indianapolis, Ind.). Plasmid DNAs from eight independent transformants was purified using Wizard™ plus Miniprep DNA Purification System (Promega, Madison, Wis.). Seven of the eight had the expected insert and clone 65-1 was chosen for subsequent analysis.

Primers for sequencing were synthesized on a 394 DNA/RNA Synthesizer (Applied Biosystems, Foster City, Calif.). The sequence of clone 65-1 is given in the Sequence Listing as SEQ ID NO:3. Clone 65-1 contained the first 233 bases of the coding region of the metallothicnein protein as predicted from the cDNA sequence.

The promoter was amplified using polymerase chain reaction from clone 65-3 and the T3 primer and primer MetNco, which is given as SEQ ID NO:4: (5' GCA CCC CAT GGC CGA TCG ACG CCT CTT AAT TTC CTC TA 3'). This introduced an NcoI restriction site for subsequent fusion of the promoter to gene coding regions. Amplification reactions were completed with the Expand™ Long Template PCR System (Boehringer Mannheim, Indianapolis, Ind.). Amplifications were cycled in microtitre plates with a 56° C. annealing temperature. Amplification products were separated and visualized by 1.0% agarose gel electrophoresis. The resulting 1800 base pair amplification product was excised from the agarose and the DNA was purified using Qiaex II (Qiagen, Hilden, Germany). The products were ligated into pCR2.1 using the Original TA Cloning Kit (Invitrogen Corporation, San Diego, Calif.). Ligations were transformed into One Shot™ INVαF' competent cells from the Original TA Cloning Kit. Plasmid DNA from eight independent transformants was isolated and seven of the eight had the expected size insert based on EcoRI digestions.

The promoter was liberated on an XbaI/NcoI fragment from clone 67-8 taking advantage of the XbaI restriction site from the TA cloning vector. The promoter was ligated into the XbaI/NcoI site of GGN/61-1 which replaced the promoter from the maize globulin S (glbS) which was fused to the β-glucuronidase (GUS) gene (Jefferson, 1986) and nopaline synthase 3' untranslated region (nos). This ligated mix was transformed into DH5α and ampicillin resistant colonies were grown on nylon membranes and screened by hybridization to labeled metallothionein promoter XbaI/NcoI fragment from clone 67-8 described above. Twenty nanograms of the gel-purified fragment was labeled with 50 µCi [α-32P]-dCTP (Amersham Corp., Arlington Heights, Ill.) using READY-TO-GO labeling beads (Pharmacia Biotech, Piscataway, N.J.) according to the manufacturer and purified over ProbeQuant™ G-50 Micro Columns (Pharmacia Biotech, Piscataway, N.J.). The labeled probe was denatured by boiling for 5 min, chilled on ice for 5 min, and added directly to the filters. Hybridization was done in ZipLoc bags (DowBrands, Indianapolis, Ind.) at 60° C. for 16 h. Blots were washed three times for 15 min. in lare excess (1000 mL) of pre-warmed washing solution [20 mM sodium phosphate pH6.5, 50 mM NaCl, 1 mM EDTA, and 0.1% SDS] at 60° C. The filters were exposed to Fuji NIF X-ray film (Stamford, Conn.) using two intensifying screens (DuPont Lightning Plus) at −70° C. for six hours. Plasmid DNA from eight of the clones which hybridized to the promoter were isolated as described above and analyzed by restriction digestion using EcoRI and NcoI enzymes. Clones MGN77-1 and MGN77-4 were chosen for DNA sequence analysis which revealed that the promoter was in the correct orientation, however there was an irregular 46 base pair deletion which began at position −185 from the ATG start codon and proceeded to base −256. This deletion was most likely introduced during the amplification reactions. To correct the sequence the 2212 base pair PinAI/KpnI fragment from MGN77-4 was ligated into the 4482 base pair PinAI/KpnI fragment of 65-1. This ligated mix was transformed into DH5α and ampicillin resistant colonies were selected. Eight of the resultant colonies were grown for DNA extraction as described above and the DNAs were analyzed by digestion with XhoI and NcoI. All clones appeared to have the correct size restriction fragments and the sequence of clone MGN111-1 was determined (SEQ ID NO:5:). The sequence from this clone appeared correct and DNA was prepared for transformation experiments.

Example 4
Transient Testing of Metallothionelnl-Gus Construct

Two plasmids, MGN111-1 (containing metallothionein promoter fused to GUS) as well as a control pDAB418 (containing ubiquitin promoter fused to GUS), were tested for transient expression in immature zygotic embryos using the 'High II' genotype (Armstrong et al. (1991) Maize Genet. Coop. News Lett. 65: 92–93.) For testing express-on, embryos 13–18 DAP were isolated and cultured on 15 Ag10 medium (Chu, C. (1978) *The N6 medium and its application to anther culture of cereal crops.* Proc. Symp. Plant Tissue Culture, Peking Press, 43–56) for 1–2 days before DNA delivery. Medium 15Ag10 consisted of N6 basal salts and vitamins, Fe-EDTA, 20 g/L sucrose, 2.9 g/L L-proline, 100 mg/L enzymatic casein hydrolysate (ECH), 1 mg/L 2,4-dichloro-phenoxyacetic acid (2,4-D), 10 mg/L silver nitrate, and 2.5 g/L GELRITE (Schweizerhall, South Plainfield, N.J.) at pH 5.8. For blasting, approximately 12 embryos were arranged in a target area of approximately 1 cm² on blasting medium and covered with a 230 µM stainless steel screen. Blasting medium differed from 15 Ag10 in that it contained 690 mg/L L-proline, 2% agar and no silver nitrate.

For blasting, 140 µg of plasmid DNA was precipitated onto 60 mg of alcohol-rinsed, spherical gold particles (1.0 µm diameter) by adding 74 µL of 2.5 M CaCl$_2$ and 30 µL of 0.1 M spermidine (free base) to 300 µL of plasmid DNA. The solution was immediately vortexed and the DNA-coated gold particles were allowed to settle. The resulting clear supernatant was removed and the gold particles were resuspended in 1 mL of absolute ethanol. This suspension was diluted with absolute ethanol to obtain 15 mg DNA-coated gold/mL (Pareddy et al., (1997) Maydica 42:143–154).

Helium blasting accelerated suspended DNA-coated gold particles towards and into the prepared tissue targets. The device used was an earlier prototype of that described in U.S. Pat. No. 5,141,131 which is incorporated herein by reference. Tissues were covered with a stainless steel screen (230 µm openings) and placed under a partial vacuum of 25 inches of Hg in the device chamber. The DNA-coated gold particles were further diluted 1:1 with absolute ethanol prior to blasting and were accelerated at the embryo target once using a helium pressure of 1500 psi, with each blast delivering 20 µL of the DNA/gold suspension.

One day after blasting, embryos were subjected to histochemical GUS analysis (Jefferson (1987) Plant Mol. Biol. Rep. 5:387–405). Briefly, tissues were placed in 24-well microtiter plates (Corning) containing 500 µL of assay buffer [0.1 M sodium phosphate, pH 8.0, 0.5 mM potassium ferricyanide, 0.5 mM potassium ferrocyanide, 10 mM sodium EDTA, 1.9 mM 5-bromo-4-chloro-3-indolyl-beta-D-glucuronide, and 0.06% TRITON X-100] per well and incubated in the dark for 1–2 days at 37° C. before analysis. GUS expression units, visualized as blue spots per target area, were counted under a microscope. The results of transient expression are presented in Table 1. In conclusion, moderate to high levels of transient expression were observed with metallothionein promoter in immature zygotic embryos of maize.

TABLE 1

Transient GUS expression of metallothionein-GUS construct in immature embryos of maize.

| Construct | Promoter | GUS Expression Units/Target |
|---|---|---|
| MGN111-1 | metallothionein | 93 |
| pDAB418 (Control) | Ubiquitin | 479 |

Example 5
Production of Stably Transformed Callus and Development of Mature Somatic Embryos To produce stable transgenic callus for in vitro maturation of somatic embryos, 'Type II' callus targets were blasted as described above. 'Type II' callus cultures were initiated from immature zygotic embryos of the genotype "Hi-II." (Armstrong et al, (1991) Maize Cooperation Newsletter, pp.92–93). Embryos were isolated from greenhouse-grown ears from crosses between Hi-II parent A and Hi-II parent B or F2 embryos derived from a self- or sib-pollination of a Hi-II plant. Immature embryos (1.5 to 3.5 mm) were cultured on initiation medium consisting of N6 salts and vitamins (Chu et al, (1978) The N6 medium and its application to anther culture of cereal crops. Proc. Symp. Plant Tissue Culture, Peking Press, 43–56) 1.0 mg/L 2,4-D, 25 mM L-proline, 100 mg/L casein hydrolysate, 10 mg/L AgNO$_3$, 2.5 g/L GELRITE, and 20 g/L sucrose, with a pH of 5.8. Selection for Type II callus took place for ca. 2–12 weeks. After four weeks callus was subcultured onto maintenance medium (initiation medium in which AgNO$_3$ was omitted and L-proline was reduced to 6 mM).

Particle preparation was performed as previously described. Afterwards, ca. 600 mg of embryogenic callus tissue was spread over the surface of Type II callus maintenance medium as described herein lacking casein hydrolysate and L-proline, but supplemented with 0.2 M sorbitol and 0.2 M mannitol as an osmoticum. Following a 4–16 h pre-treatment, tissue was transferred to culture dishes containing blasting medium (osmotic media solidified with 20 g/L tissue culture agar (JRH Biosciences, Lenexa, Kans.) instead of 7 g/L GELRITE (Schweizerhall)). Helium blasting was performed as described herein. Immediately post-blasting, the tissue was transferred to osmotic media for a 16–24 h recovery period. Afterwards, the tissue was divided into small pieces and transferred to selection medium (maintenance medium lacking casein hydrolysate and L-proline but having 30 mg/L BASTA (Agrevo)). Every four weeks for 3 months, tissue pieces were non-selectively transferred to fresh selection medium. After 6 weeks and up to 20 weeks, callus sectors found proliferating against a background of growth-inhibited tissue were removed and isolated. The resulting BASTA-resistant tissue was subcultured biweekly onto fresh selection medium.

From these stably transformed cultures, somatic embryos were made to develop as seed embryos by growing embryogenic callus on MS medium containing 6% (w/v) sucrose. The callus was grown for 7 days and then somatic embryos were individually transferred to MS medium with 6% sucrose and 10 μM abscisic acid, hereinafter ABA.

Example 6
Stable Testing of Metallothionein-Gus Expression in Mature Somatic Embryos A. A total of 190 'Type II' embryogenic callus targets were blasted as described herein (Pareddy et al. (1997) Maydica 42:143–154) cobombarding pDAB308 (35T-bar) and MGN 111–1 (Metallothioneinl-GUS). Using Basta® selection, forty two Basta®-resistant colonies were produced. Callus of about 32 transgenic lines were transferred to embryo maturation media with or without ABA for development of somatic embryos using the procedure described previously. After 14 days of culture, somatic embryos of different transgenic lines were subjected to histochemical GUS assay as described herein. Out of 32 lines tested, 14 showed GUS expression. Although intensity of GUS expression varied from line to line, moderate to high levels of expression were observed in a few lines as shown in Table 2.

B. Southern Analysis of Met Transgenic Maize Callus

Transgenic callus was analyzed for the presence of the integrated GUS gene by Southern analysis. Callus material was removed from the media and soaked in distilled water for 30 minutes prior to lyophilization. Genomic DNA from callus was prepared from lyophilized tissue as described by Saghai-Maroof et al. (1984) Proc. Natl. Acad. Sci. U. S. A. 81: 8014–8018. Eight micrograms of each DNA was digested with the restriction enzymes EcoRI and KpnI using conditions suggested by the manufacturer (Bethesda Research Laboratory, Gaithersburg, Md.) and separated by agarose gel electrophoresis. The DNA was blotted onto nylon membrane as described by Southern, E. (1975) J. Molec. Biol. 98, 503 and Southern, E. (1980) Methods of Enzymol. 69, 152.

A probe specific for β-glucuronidase (GUS) coding region was excised from the pDAB418 plasmid using the restriction enzymes NcoI and SstI. The resulting 1.9 kb fragment was purified with the Qiaex II DNA purification kit (Qiagen Inc., Chatsworth, Calif.). The probe was prepared using the Ready To Go DNA labeling beads (Pharmacia LKB, Piscataway, N.J.) with 50 microcuries of $\alpha^{32}$P-dCTP (Amersham Life Science, Arlington Heights, Ill.). The GUS probe was hybridized to the genomic DNA on the blots overnight at 60° C. The blots were washed at 60° C. in 0.25× SSC and 0.2% SDS for 45 minutes, blotted dry and exposed to XAR-5 film overnight with two intensifying screens.

Fifteen transgenic MGN callus lines were characterized by Southern analysis. Genomic DNA was digested with the restriction enzymes EcoRI and KpnI which should result in a 3.8 kb fragment when hybridized to a probe specific for the GUS coding region. The 3.8 kb hybridization product should consist of the metallothionein promoter, β-glucuronidase coding region and nopaline synthase 3' UTR. Ten of the fifteen callus lines analyzed contained an intact gene construct as evident by the 3.8 kb hybridization product. Four lines had moderate integration events having two or three hybridization products present. Six lines had complex integration events containing more than three and as many as thirteen hybridization products. Results for the Southern analysis are summarized for the transgenic callus lines in Table 2.

Example 7
Regeneration of Transgenic Plants and Testing of Metallothionein-Gus Expression A. Regeneration was initiated by transferring callus tissue to cytokinin-based induction medium, which consisted of Murashige and Skoog salts, hereinafter MS salts, and vitamins (Murashige and Skoog, (1962) Physlol. Plant. 15:473–497) 30 g/L sucrose, 100 mg/L myo-inositol, 30 g/L mannitol, 5 mg/L 6-benzylaminopurine, hereinafter BAP, 0.025 mg/L 2,4-D, 30 mg/L BASTA, and 2.5 g/L GELRITE (Schweizerhall) at pH 5.7. The cultures were placed in low light (125 ft-candles) for one week followed by one week in high light (325 ft-candles). Following a two week induction period, tissue was non-selectively transferred to hormone-free regeneration medium, which was identical to the induction medium except that it lacked 2,4-D and BAP, and was kept in high light. Small (1.5–3 cm) plantlets were removed and placed in 150×25 mm culture tunes containing SH medium (SH salts and vitamins (Schenk and Hildebrandt, (1972) Can. J. Bot. 50:199-204), 10 g/L sucrose, 100 mg/L myo-inositol, 5 mL/L FeEDTA, and 2.5 g/L GELRITE (Schweizerhall), pH 5.8). Plantlets were transferred to 10 cm pots containing approximately 0.1 kg of METRO-MIX 360 (The Scotts Co. Marysville, Ohio) in the greenhouse as soon as they exhibited growth and developed a sufficient root system. They were grown with a 16 h photoperiod supplemented by a combination of high pressure sodium and metal halide lamps, and were watered as needed with a combination of three independent Peters Excel fertilizer formulations (Grace-Sierra Horticultural Products Company, Milpitas, Calif.). At the 3–5 leaf stage, plants were transferred to five gallon pots containing approximately 4 kg METRO-MIX 360.

B. Southern Analysis of Transgenic Plants

Southern analysis was completed on plant tissue to confirm the presence of the intact GUS gene fusion. Leaf material was harvested from as many as four plants per $R_0$ line when they reached the 6–8 leaf stage. Genomic DNA from $R_0$ plants was prepared from lyophilized tissue as described above. Four MGN $R_0$ lines were characterized by Southern analysis. Genomic DNA was digested with the restriction enzymes EcoRI and KpnI which should result in a 3.8 kb fragment when hybridized to a probe specific for the GUS coding region. The 3.8 kb hybridization product should consist of the metallothionein promoter, β-glucuronidase coding region and nopaline synthase 3' UTR. Three of the four $R_0$ lines analyzed contained an intact gene construct as evident by the 3.8 kb hybridization product. All four of the lines had complex integration events containing more than three and as many as ten hybridization products. Southern results of plants from the four of the transgenic lines are summarized in Table 2.

TABLE 2

GUS expression in mature somatic embryos of different Metallothionein1-GUS transgenic lines of maize.

| | Histochemical GUS Expression | | Presence of Hybridizing DNA | |
|---|---|---|---|---|
| Transgenic Line | Present/ Absent | Level | Callus | $R_0$ Plants |
| 308/Met1-02 | No | NA | No | NT |
| 308/Met1-05 | Yes | Low | Yes | NT |
| 308/Met1-12 | Yes | Low | Yes | NT |
| 308/Met1-14 | Yes | Low | Yes | NT |
| 308/Met1-15 | Yes | Moderate | Yes | NT |
| 308/Met1-16 | Yes | High | NT | Yes |
| 308/Met1-28 | Yes | High | Yes | Yes |
| 308/Met1-31 | Yes | High | Yes | NT |
| 308/Met1-35 | Yes | Low | NT | No |
| 308/Met1-43 | No | NA | No | NT |
| 308/Met1-44 | Yes | Low | NT | Yes |

In Table 2, "Level" refers to complexity of hybridization products, and "NT" means not tested Example 8
Pollination and GUS Analysis of Transgenic Plants
A. Primary regenerants ($R_0$ plants) were self- or sib-pollinated when possible after an additional 6–10 weeks in five gallon pots, and $R_1$ seed was collected at 40–45 days post-pollination. When self- or sib-pollinations were not possible, plants were outcrossed to elite inbreds. These kernels were then planted in five gallon pots to obtain $R_1$ plants which were either selfed or outcrossed to elite inbreds to produce $R_2$ seed.

For further analysis of metallothionein-GUS expression, plants were regenerated from 9 independent transgenic lines. $R_0$ plants from four lines (pDAB308/Metl-16, 28, 35, 44) were grown to maturity and controlled pollinations (self, sib, or cross with CQ806) were made as described herein. Histochemical analysis of leaf and/or root from both Ro and $R_1$ plants from said plants (i.e., pDAB308/Metl-28) was negative. However, embryos from the seed produced by said plant at 25 DAP exhibited low to high levels of GUS expression. (Table 3). Although GUS expression was seen in aleurone layer, no expression was observed in endosperm.

TABLE 3

GUS expression in different tissues of Metallothionein-GUS transgenic plants.

| | Histochemical GUS Expression | | | | |
|---|---|---|---|---|---|
| Transgenic Line | Embryo | Aleurone Layer | Endosperm | Leaf* | Root* |
| pDAB308/Met1-16 | Yes | Yes | No | NT | NT |
| pDAB308/Met1-28 | Yes | Yes | No | No | No |
| pDAB308/Met1-35 | Yes | Yes | No | NT | NT |
| pDAB308/Met1-44 | Yes | Yes | No | NT | NT |

NT: not tested
*$R_1$ plants

B. GUS Analysis in Embryos

Embryos from 308/Met-16-04, 308/Met-28-01, 308/Met-44-11, CQ806 (negative control) and UGN-28-05 and UGN-40-05 (positive controls) plants, which were pollinated by outcrossing to inbred CQ806, and examined histochemically for GUS expression. Embryos were harvested from ears 7 and 31 days after pollination (DAP). GUS expression was determined histochemically as described by Jefferson (1987) Plant Mol. Blol. Rep. 5:387–405. Results are summarized in Table 4. No GUS expression was observed in the embryos from the negative control plants. Expression was observed in all embryos analyzed from the lines transformed with the positive control plasmid, UGN81-3 (positive control), which contains the GUS gene driven by the promoter from the maize ubiquitin 1 gene. The initiation of expression was variable in the individual lines transformed with pMGN111-1, which contains GUS driven by the metallothionein promoter. Expression was observed as early as 10 days after pollination (DAP) in line 308/MET1-28 and as late as 20 DAP in line 308/Met-44. Expression in all MET lines continued through maturity at 31 DAP.

TABLE 4

GUS Expression In Transgenic Maize Embryos Evaluated Histochemically.

| | Plant | GUS Histochemical Results (after 24 hours) | | | | | | | | |
|---|---|---|---|---|---|---|---|---|---|---|
| | | 7 DAP | 10 DAP | 13 DAP | 16 DAP | 19 DAP | 22 DAP | 25 DAP | 28 DAP | 31 DAP |
| A | Negative control | nt | − | − | − | − | − | − | − | − |
| D | UGN-28.05.05 | + | + | + | + | + | + | + | + | + |
| E | UGN-40-05.07 | + | + | + | + | + | + | + | + | + |
| F* | 308/MET1-44-11.07 | nt | nt | nt | − | − | + | + | + | + |
| G | 308/MET1-16-4.06 | nt | − | − | − | + | + | + | + | + |
| H | 308/MET1-28-10.04 | − | + | + | + | + | + | + | + | + | nt = not tested
*positive at 20 DAP

C. GUS Analysis in Roots and Leaves

Plant tissues from transgenic lines 308/Met-16-04, 308/Met-28-10 and 308/Met44-11 were grown and prepared for quantitative evaluation of GUS expression. In addition, samples were collected from the maize inbred CQ806, which was used as a negative control for these experiments. Samples were also collected and tested from transgenic lines UGN-40-05 and UGN-28-05, which had been transformed with the plasmid pUGN81-3 and serves as a positive control for expression. Leaf and root tissue from $R_1$ transgenic plants at the V6 (six leaves) stage were collected, frozen in liquid nitrogen and ground to a fine powder with a mortar and pestle. Samples were weighed into 50 mL centrifuge tubes. Per gram of sample, four mLs of GUS-Light™ (Tropix, Bedford, Mass.) extraction buffer, modified by the addition of 20% glycerol, 1.0% polyvinylpolypyrolidone and 7 ml/mL b-mercaptoethanol were added to each sample and the sample was homogenized for two 10 second intervals. Samples were maintained on ice throughout the extraction protocol and clarified by centrifugation at 3000 rpm and 5° C.for 5 minutes. Two one mL aliquots of supernatant were transferred to sterile microfuge tubes and re-centrifuged at full speed (Eppendorf Centrifuge Model 5415). Supernatant was again removed to fresh tubes and stored at −70° C. until ready for analysis.

Protein concentrations were determined based on the Bradford method using dye reagent from Bio-Rad (Hercules) and 30 mg/dL human serum albumin protein standard (Sigma, St. Louis, Mo.). For analysis of GUS activity, a GUS-Light™ assay kit (Tropix, Bedford, Mass.) was used. Both aliquots of each sample were tested in duplicate, using a total of 10 mL of extract plus extract buffer per luminometer vial. GUS-Light™ Reaction Buffer was prepared from the assay kit by diluting liquid Glucuron™ substrate according to the manufacturer's instructions. This buffer was warmed to room temperature and added in 190 μL aliquots to each luminometer vial at 10-second intervals. After a one hour incubation at room temperature, 300 μL of GUS-Light™ Light Emission Accelerator Buffer was added and luminescence was detected over a 5-second integration period. "Blank reactions" (using 10 ml of extraction buffer) and E. coli-derived β-glucuronidase standard were also included in the GUS assay. GUS activity was reported as relative light units (RLU)/mg protein.

D. GUS expression in Leaves and Roots.

No significant GUS expression was observed in the leaves or roots of either 308/Met-16-04, 308/Met-28-10 or 308/Met-44-11 plants (Table 5). GUS expression was observed in the plants transformed with pUGN81-3 where the GUS gene was driven by the maize 10 Ubil promoter. These results confirm the observation that the maize metallothionein promoter is not expressed in the leaves or roots of the plants, and is therefore embryo specific.

TABLE 5

Results of GUS-Light ™ analysis of leaves of roots and plants transformed with MGN111-1 plasmid.

| Transgenic Plant | | Histochemical GUS Expression (RLU/ug protein) | |
|---|---|---|---|
| Line | Plasmid | leaf | root |
| CQ806(1)[1] | none | 44 | 34 |
| CQ806(2)[1] | none | 40 | 13 |
| UGN-28-05.01[2] | pUGN81-3 | 4858 | 26528 |
| UGN-28-05.02[2] | pUGN81-3 | 4143 | 20870 |
| UGN-40-05.01[2] | pUGN81-3 | 100281 | 154941 |
| UGN-40-05.02[2] | pUGN81-3 | 91209 | 102148 |
| 308/Met-16-04.01 | pMGN111-1 | 22 | 190 |
| 308/Met-16-04.02 | pMGN111-1 | 7 | 50 |
| 308/Met-28-10.01 | pMGN111-1 | 10 | 38 |
| 308/Met-28-10.02 | pMGN111-1 | 7 | 64 |
| 308/Met-44-11.01 | pMGN111-1 | 7 | 41 |
| 308/Met-44-11.02 | pMGN111-1 | 7 | 25 |

[1]CQ806 is negative control
[2]UGN transgenic plants serve as positive controls

Description of Plasmids

A. Description of pDAB308

The features of pDAB 308 are described in the following table

| Features of pDAB 308 | |
|---|---|
| bp of pDAB308 | Description of feature |
| 1–19 | linker including PstI site and BglII site |
| 20–271 | correspond to bp 7093–7344 of the Cauliflower Mosaic Virus CabbS strain, hereinafter CaMV, (Franck, et al., (1980) Cell 21:285–294) |
| 272–279 | linker including ClaI site |
| 280–626 | correspond to bp 7093–7439 of CaMV |
| 627–646 | linker including XbaI site and BamHI site |
| 647–666 | correspond to bp 167–186 of Maize Streak Virus, hereinafter MSV, (Mullineaux, et al., (1984) EMBO J. 3:3063–3068) |
| 667–756 | correspond to bp 188–277 of MSV |
| 757–849 | bases CA followed by bp 120–210 of maize alcohol dehydrogenase 1S, hereinafter Adh1, (Dennis, et al., (1984) Nucl. Acids Res. 12:3983–4000) containing parts of exon 1 and intron 1 |
| 850–967 | correspond to bp 555–672 of Adh1 containing parts of intron 1 and exon 2 |
| 968–977 | linker |
| 978–1017 | 278–317 of MSV |
| 1018–1566 | a modified BAR coding region from pIJ4104 (White et al., (1990) Nucl. Acids. Res. 18:1062) having the AGC (serine) codon in the second position replaced by GCC (alanine) and nucleotide 546 changed from G to A |
| 1567–1590 | linker including BglII and SacI sites |
| 1591–1847 | correspond to bp 1298 to 1554 of nopaline synthase (DePicker, et al., (1982) J. Molec. Appl. Genet. 1:561–573) |
| 1848–4496 | G followed by the rest of pUC 19 |

B. Description of pDAB418

The maize expression vector, pDAB418, containing the ubiquitin promoter regulatory element driving the b-glucuronidase gene was used in the expression studies. In addition this plasmid carries a second gene which serves as a plant selectable marker. Plasmid pDAB418 is a 10149 base pair double stranded plant transformation vector, the features of which are described in the following table:

| bp of pDAB418 | description of feature |
|---|---|
| 1–31 | linker sequence including an EagI site and HindIII site |
| 32–2023 | maize ubiquitin (Ubi1) promoter and first intron that were PCR amplified from genomic DNA of maize genotype B73 (Christensen et al., (1992) Plant Mol. Biol. 18:675–689) |
| 2024–2042 | linker including KpnI site, SmaI site, and SalI site |
| 2043–3894 | correspond to bp 2551–4402 of plasmid pBI101 (Clontech, Palo Alto, CA) |
| 3895–3904 | linker |
| 3905–4174 | correspond to bp 4414–4683 of pBI101 |
| 4175–4192 | linker including HindIII site |
| 4193–6184 | a second copy of the maize ubiquitin promoter and intron sequence described above |
| 6185–6196 | linker |
| 6197–6753 | correspond to bp 29–585 of the phosphinotricin acetyl transferase (BAR) gene of *Streptomyces hygroscopicus* (White et al., (1989) Nucleic Acids Res. 18:1062). To facilitate cloning, nucleotides 34 and 575 of the published sequence were changed from A to G and G to A, respectively. |
| 6754–6758 | linker |
| 6759–7472 | correspond to bp 21728 through 22441 from the *Agrobacterium tumefaciens* octopine Ti plasmid pTi15955 (Barker et al. (1983) Plant Mol. Biol. 2, 335–350. |
| 7473–7504 | polylinker including EcoRI, ClaI, EcoRV, XbaI, and SacI sites |
| 7505–10149 | reverse compliment of nucleotides from the plasmid backbone which was derived from pUC19 (Yanish-Perron et al., (1985) Gene 33:103–119) |

C. Description of pUGN81-3

The maize expression vector, pUGN81-3, containing the ubiquitin promoter regulatory element driving the B-glucuronidase gene was used in the expression studies. Plasmid pUGN81-3 is a 8730 base pairs double stranded plant transformation vector having the features described in the following table:

| bp of pUGN81-3 | description of feature |
|---|---|
| 1–17 | polylinker including SacII and PstI sites |
| 18–2003 | maize ubiquitin promoter and first intron that were PCR amplified from genomic DNA of maize genotype B73 (Christensen et al., (1992) Plant Mol. Biol. 18:675–689) |
| 2004–2002 | polylinker including KpnI, SmaI, and SalI sites |
| 2023–4154 | correspond to bp 2551–4682 of plasmid pBI101 (Clontech, Palo Alto, CA) |
| 4155–4197 | polylinker including HindIII, SphI, PstI, and NaeI sites |
| 4198–4264 | linker |
| 4265–4516 | correspond to bp 7093–7344 of the Cauliflower Mosaic Virus genome (Franck et al., (1980) Cell 21:285–294). |
| 4517–4524 | linker |
| 4525–4776 | duplication of nucleotides 4254 to 4516 |
| 4777–4871 | correspond to bp 7345–7439 of the Cauliflower Mosaic Virus genome (Franck et al., (1980) Cell 21:285–294). |
| 4872–4891 | linker |
| 4892–5001 | correspond to bp 167 to 277 of the Maize Streak Virus genome with base 187 absent (Mullineaux at al., (1984) EMBO J. 3:3063–3068). |
| 5002–5223 | modified first intron of the maize alcohol dehydrogenase gene (Adh1-S) (Dennis et al., (1984) Nucleic Acids Res. 12:3983–4000). The modification resulted in removal of 343 nucleotides (bases 1313 to 1656) with bases 1222 to 1312 (intron 5' end) and nucleotides 1657 to 1775 (intron 3' end) of the maize Adh1-S gene remaining |
| 5224–5257 | correspond to bp 279–312 of Maize Streak Virus (MSV) |
| 5258–5814 | correspond to bp 29–585 of the phosphinotricin acetyl transferase (BAR) gene of *Streptomyces hygroscopicus* (White et al., (1989) Nucleic Acids Res. 18:1062). To facilitate cloning, nucleotides 34 and 575 of the published sequence were changed from A to G and G to A, respectively. |
| 5815–5819 | linker |
| 5820–6089 | correspond to bp 4414–4683 of plasmid pBI101 (Clontech, Palo Alto, CA) |
| 6090–6094 | linker |
| 6095–8730 | reverse compliment of nucleotides from the plasmid backbone which was derived from pUC19 (Yanish-Perron et al., (1985) Gene 33:103–119). |

We claim:

1. An isolated DNA molecule comprising base pairs 50 to 1649 of SEQ ID NO:5.

2. An expression cassette comprising an embryo specific promoter operably linked to a heterologous nucleic acid sequence wherein the promoter comprises a sequence extending from about base pair 50 to base pair 1649 of SEQ ID NO:5.

3. A method of expressing a heterologous nucleic acid sequence in a plant comprising:
   a) introducing into a plant cell a vector comprising an embryo specific maize metallothionein promoter operably linked to the heterologous nucleic acid sequence wherein the promoter comprises a sequence extending from about base pair 50 to base pair 1649 of SEQ ID NO:5; and
   b) regenerating a plant from said cell.

4. A method of producing seed comprising:
   a) introducing into a plant cell a vector comprising an embryo specific maize metallothionein promoter, wherein the promoter comprises a sequence extending from about base pair 50 to base pair 1649 of SEQ ID NO:5, operably linked to a heterologous nucleic acid sequence;
   b) regenerating a plant from said cell; and
   c) sexually transmitting said embryo specific maize metallothionein promoter operably linked to said heterologous nucleic acid sequence to progeny.

5. The method of producing seed of claim 4 including the additional step collecting the seed produced by said progeny.

* * * * *

SEQUENCE LISTING

<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: SK primer

<400> SEQUENCE: 1
cgctctagaa ctagtggatc                                          20

<210> SEQ ID NO 2
<211> LENGTH: 565

```
<212> TYPE: DNA
<213> ORGANISM: Zea mays
<220> FEATURE:
<221> NAME/KEY: CDS
<222> LOCATION: (94)..(324)

<400> SEQUENCE: 2
agctccccca acgctactac cgccgctagc tggttcaagt gcggcgagcg g agccggaga          60 ccggtagagg aaattaagag gcgtcgatcg ggc atg ggg tgc g ac gac aag tgc         114
                                    Met Gly Cys Asp Asp Lys Cys
                                      1               5 ggg tgc gcc gtg ccg tgc ccc ggc ggc aag g ac tgc agg tgc acg tcg          162
Gly Cys Ala Val Pro Cys Pro Gly Gly Lys A sp Cys Arg Cys Thr Ser
         10                  15                  20 ggg agc ggc ggg cag cgg gag cac acg act t gc ggc tgc ggg gag cac          210
Gly Ser Gly Gly Gln Arg Glu His Thr Thr C ys Gly Cys Gly Glu His
 25                  30                  35 tgc gag tgc agc ccg tgc acg tgt ggc cgg g cc acg atg ccg tcc ggc          258
Cys Glu Cys Ser Pro Cys Thr Cys Gly Arg A la Thr Met Pro Ser Gly
 40                  45                  50                  55 cgc gag aac agg agg gct aac tgc tcc tgc g gg gcg tcc tgc aac tgc          306
Arg Glu Asn Arg Arg Ala Asn Cys Ser Cys G ly Ala Ser Cys Asn Cys
                 60                  65                  70 gca tcc tgc gcc tcg gcc tgatccgtgc gcctcgccct c gtgctaccg                 354
Ala Ser Cys Ala Ser Ala
                 75 cgctgcctag tggagggagt tgtctagtga ggctggagac gaagcaacta g cactacttc        414 taataaaggg cttgtgtcat gctcgccaga cgcatcacgc gctgcatctg c atcgtggta        474 tcgtgtagta agtttgtgta tgaataaaca ctaccacttt atgtttcgca a aaaaaaaa         534 aaaaaaaaaa aaaaaaaaaa aaaaaaaaaa a                                        565

<210> SEQ ID NO 3
<211> LENGTH: 1843
<212> TYPE: DNA
<213> ORGANISM: Zea mays
<220> FEATURE:
<221> NAME/KEY: CDS
<222> LOCATION: (1601)..(1831)

<400> SEQUENCE: 3
gaattcctat gagcaaagaa gagaaaatct tttatgagaa gtgggttggg a gaaaaccat         60 cactttcata cttgcgcaca tgggggtgc atggcgaaag tcagtgtacc a attaataaa        120 aagtgcaagc ttggacaagg atagtggatt gtatctttct agattatgct t cctgtagca       180 tagcttatag atttttagta gttaaaactg acgctcctga tgtgtatgta g ataccatta       240 tagaatctcg cgatgctact ttctttgaaa acatatatcc agtaaaagac a ttcatagca       300 attctagata ttcttctgag ataactcctg aacataatgc acatgttgag a gttttgaac       360 aaccacataa gaatgtccta gaggaggatg acaacgatgc tcctaaaagg a gcaagatac       420 aaagggttga caaatccttt ggtgatgatt tcattatgta ccttgtggac g acactccta       480 ctactattac ggaagcattt gcatctccat ataaagatga ttggaaagaa g catttcaga       540 atgatatgga ctcaattctt tcaaatggta gatgggaggt cactgattga c cctatggtt      600 gtaaacctgt gggttgtaag cggctgttta aaagaagct caagtctgat g cacaatcg        660 agaagtacaa ggctaggctt gtgactaaag gctatgctca gaaagaatga g aagcttct       720 ttaatactta tttacctgtt gctagaatgt ctactattcg agtactattt t ccttggctt      780
```

-continued

```
gcaaccttta gagaacgatt catatgggta gcagtgtgtt ttaaatttta c actataata    840 tttaaggatc agatcagatt aggatcgagc tctatttta ttcattttta a actaaaatt     900 tattcagagt tatatcattt tgtgaagaag tatttggatc acgataaatt a catcgtcat   960 caatctaatg gcgtaaaata aacgtcgacg tggacagtgt aaatgcgcag c ttggtacac   1020 aacctttact atgtaaataa ataaattctg aatctgctag ctcctgcaga t atccatgcg   1080 aagcgacaat tcagagcaag cttagcggcc actgccaggt ctagtagtat t taccatttc   1140 atccaattct ccgaagcaaa ggccttctag cgggccaact tcctttacct g ctgatggac   1200 cggcgtaggc tatcgcggac aggcagcggg acttcttctc ctcatgggcc g ttcgactcc   1260 ggcctatttt tcgtcgtcag cgacagcgtc aggggataa gaacgctcga g caaggtatc    1320 atcccgacat catcccgcgc cgcggccggg accgcgtgt cccaccacct g tcgacgcgg    1380 cgtgggagac gtgcgccgcg tgcgtgcgcg tcgccgcccg gccgttctag a cctgtagac   1440 cttgggctc tggagctcca ttatatacag aggcaagtgg gagccgtttg t tcagcagcg    1500 ctacttgtgc tcccccaacg ctactaccgc cgctagctgg ttcaagtgcg g cgagcggag   1560 ccggagaccg gtagaggaaa ttaagaggcg tcgatcgggc atg ggg t gc gac gac      1615
                                             Met Gly Cys Asp Asp
                                              1               5 aag tgc ggg tgc gcc gtg ccg tgc ccc ggc g gc aaa gac tgc agg tgc      1663
Lys Cys Gly Cys Ala Val Pro Cys Pro Gly G ly Lys Asp Cys Arg Cys
         10                  15                  20 acg tcg ggg agc ggc ggg cag cgg gag cac a cg act tgc ggc tgc ggg      1711
Thr Ser Gly Ser Gly Gln Arg Glu His T hr Thr Cys Gly Cys Gly
     25                  30                  35 gag cac tgc gag tgc agc ccg tgc acg tgt g gc cgg gcc acg atg ccg      1759
Glu His Cys Glu Cys Ser Pro Cys Thr Cys G ly Arg Ala Thr Met Pro
 40                  45                  50 tcc ggc cgc gag aac agg agg gct aac tgc t cc tgc ggg gcg tcc tgc     1807
Ser Gly Arg Glu Asn Arg Arg Ala Asn Cys S er Cys Gly Ala Ser Cys
     55                  60                  65 aac tgc gca tcc tgc gcc tcg gcc tgatccgaat t c                        1843
Asn Cys Ala Ser Cys Ala Ser Ala
 70                  75

<210> SEQ ID NO 4
<211> LENGTH: 38
<212> TYPE: DNA
<213> ORGANISM: Artificial Sequence
<220> FEATURE:
<223> OTHER INFORMATION: Description of Artificial   Sequence: T3 primer

<400> SEQUENCE: 4
gcaccccatg gccgatcgac gcctcttaat ttcctcta                             38

<210> SEQ ID NO 5
<211> LENGTH: 6694
<212> TYPE: DNA
<213> ORGANISM: Zea mays

<400> SEQUENCE: 5
ccaccgcggt ggcggccgct ctagaactag tggatccccc gggctgcagg a attcctatg    60 agcaaagaag agaaatcttt ttatgagaag tgggttggga gaaaaccatc a ctttcatac   120 ttgcgcacat gggggtgca tggcgaaagt cagtgtacca attaataaaa a gtgcaagct    180 tggacaagga tagtggattg tatctttcta aattatgctt cctgtagcat a gcttataga   240 tttttagtag ttaaaactga cgctcctgat gtgtatgtag ataccattat a gaatctcgc   300
```

```
gatgctactt tctttgaaaa catatatcca gtaaaagaca ttcatagcaa t tctagatat      360 tcttctgaga taactcctga acataatgca catgttgaga gttttgaaca a ccacataag      420 aatgtcctag aggaggatga caacgatgct cctaaaagga gcaagataca a agggttgac      480 aaatcctttg gtgatgattt cattatgtac cttgtggacg acactcctac t actattacg      540 gaagcatttg catctccata taaagatgat tggaaagaag catttcagaa t gatatggac      600 tcaattcttt caaatggtag atgggaggtc actgattgac cctatggttg t aaacctgtg      660 ggttgtaagc ggctgtttaa aaagaagctc aagtctgatg gcacaatcga g aagtacaag      720 gctaggcttg tgactaaagg ctatgctcag aaagaatgag aagacttctt t aatacttat      780 ttacctgttg ctagaatgtc tactattcga gtactatttt ccttggcttg c aacctttag      840 agaacgattc atatgggtag cagtgtgttt taaattttac actataatat t taaggatca      900 gatcagatta ggatcgagct ctattttat tcatttttaa actaaaattt a ttcagagtt      960 atatcatttt gtgaagaagt atttggatca cgataaatta catcgtcatc a atctaatgg     1020 cgtaaaataa acgtcgacgt ggacagtgta atgcgcagc ttggtacaca a cctttacta     1080 tgtaaataaa taaattctga atctgctagc tcctgcagat atccatgcga a gcgacaatt     1140 cagagcaagc ttagcggcca ctgccaggtc tagtagtatt taccatttca t ccaattctc     1200 cgaagcaaag gccttctagc gggccaactt cctttacctg ctgatggacc g gcgtaggct     1260 atcgcggaca ggcagcggga cttcttctcc tcatgggccg ttcgactccg g cctattttt     1320 cgtcgtcagc gacagcgtca gggggataag aacgctcgag caaggtatca t cccgacatc     1380 atcccgcgcc gcgccggggg accgcgtgtc ccaccacctg tcgacgcggc g tgggagacg     1440 tgcgccgcgt gcgtgcgcgt cgccgcccgg ccgttctaga cctgtagacc t tggggctct     1500 ggagctccat tatatacaga ggcaagtggg agccgtttgt tcagcagcgc t acttgtgct     1560 cccccaacgc tactaccgcc gctagctggt tcaagtgcgg cgagcggagc c ggagaccgg     1620 tagaggaaat taagaggcgt cgatcggccc atggtccgtc ctgtagaaac c ccaacccgt     1680 gaaatcaaaa aactcgacgg cctgtgggca ttcagtctgg atcgcgaaaa c tgtggaatt     1740 gatcagcgtt ggtgggaaag cgcgttacaa gaaagccggg caattgctgt g ccaggcagt     1800 tttaacgatc agttcgccga tgcagatatt cgtaattatg cgggcaacgt c tggtatcag     1860 cgcgaagtct ttataccgaa aggttgggca ggccagcgta tcgtgctgcg t ttcgatgcg     1920 gtcactcatt acggcaaagt gtgggtcaat aatcaggaag tgatggagca t cagggcggc     1980 tatacgccat ttgaagccga tgtcacgccg tatgttattg ccgggaaaag t gtacgtatc     2040 accgtttgtg tgaacaacga actgaactgg cagactatcc cgccgggaat g gtgattacc     2100 gacgaaaacg gcaagaaaaa gcagtcttac ttccatgatt tctttaacta t gccggaatc     2160 catcgcagcg taatgctcta caccacgccg aacacctggg tggacgatat c accgtggtg     2220 acgcatgtcg cgcaagactg taaccacgcg tctgttgact ggcaggtggt g gccaatggt     2280 gatgtcagcg ttgaactgcg tgatgcggat caacaggtgg ttgcaactgg a caaggcact     2340 agcgggactt tgcaagtggt gaatccgcac ctctggcaac cgggtgaagg t tatctctat     2400 gaactgtgcg tcacagccaa aagccagaca gagtgtgata tctacccgct t cgcgtcggc     2460 atccggtcag tggcagtgaa gggcgaacag ttcctgatta ccacaaaacc g ttctacttt     2520 actggctttg gtcgtcatga agatgcggac ttacgtggca aaggattcga t aacgtgctg     2580 atggtgcacg accacgcatt aatggactgg attggggcca actcctaccg t acctcgcat     2640
```

-continued

```
taccccttacg ctgaagagat gctcgactgg gcagatgaac atggcatcgt g gtgattgat    2700 gaaactgctg ctgtcggctt taacctctct ttaggcattg gtttcgaagc g ggcaacaag    2760 ccgaaagaac tgtacagcga agaggcagtc aacgggaaaa ctcagcaagc g cacttacag    2820 gcgattaaag agctgatagc gcgtgacaaa aaccacccaa gcgtggtgat g tggagtatt    2880 gccaacgaac cggatacccg tccgcaagtg cacgggaata tttcgccact g gcggaagca    2940 acgcgtaaac tcgacccgac gcgtccgatc acctgcgtca atgtaatgtt c tgcgacgct    3000 cacaccgata ccatcagcga tctctttgat gtgctgtgcc tgaaccgtta t tacggatgg    3060 tatgtccaaa gcggcgattt ggaaacggca gagaaggtac tggaaaaaga a cttctggcc    3120 tggcaggaga aactgcatca gccgattatc atcaccgaat acggcgtgga t acgttagcc    3180 gggctgcact caatgtacac cgacatgtgg agtgaagagt atcagtgtgc a tggctggat    3240 atgtatcacc gcgtctttga tcgcgtcagc gccgtcgtcg gtgaacaggt a tggaatttc    3300 gccgattttg cgacctcgca aggcatattg cgcgttggcg gtaacaagaa a gggatcttc    3360 actcgcgacc gcaaaccgaa gtcggcggct tttctgctgc aaaaacgctg g actggcatg    3420 aacttcggtg aaaaaccgca gcaggaggc aaacaatgaa tcaacaactc t cctggcgca    3480 ccatcgtcgg ctacagcctc ggtggggaat tggagctcga atttccccga t cgttcaaac    3540 atttggcaat aaagtttctt aagattgaat cctgttgccg gtcttgcgat g attatcata    3600 taatttctgt tgaattacgt taagcatgta ataattaaca tgtaatgcat g acgttattt    3660 atgagatggg tttttatgat tagagtcccg caattataca tttaatacgc g atagaaaac    3720 aaaatatagc gcgcaaacta ggataaaatta tcgcgcgcgg tgtcatctat g ttactagat    3780 cgatcgggaa ttaagcttat cgataccgtc gacctcgagg ggggcccggt a cccaattcg    3840 ccctatagtg agtcgtatta caattcactg gccgtcgttt tacaacgtcg t gactgggaa    3900 aaccctggcg ttacccaact taatcgcctt gcagcacatc ccccttcgc c agctggcgt    3960 aatagcgaag aggcccgcac cgatcgccct tcccaacagt tgcgcagcct g aatggcgaa    4020 tggcgcgaaa ttgtaaacgt taatattttg ttaaaattcg cgttaaattt t tgttaaatc    4080 agctcatttt ttaaccaata ggccgaaatc ggcaaaatcc cttataaatc a aaagaatag    4140 accgagatag ggttgagtgt tgttccagtt tggaacaaga gtccactatt a agaacgtg    4200 gactccaacg tcaaagggcg aaaaaccgtc tatcagggcg atgccccact a cgtgaacca    4260 tcaccctaat caagttttttt ggggtcgagg tgccgtaaag cactaaatcg g aaccctaaa    4320 gggagccccc gatttagagc ttgacgggga agccggcga acgtggcgag a aaggaaggg    4380 aagaaagcga aaggagcggg cgctagggcg ctggcaagtg tagcggtcac g ctgcgcgta    4440 accaccacac ccgccgcgct taatgcgccg ctacagggcg cgtcccaggt g cacttttc    4500 ggggaaatgt gcgcggaacc cctatttgtt tatttttcta aatacattca a atatgtatc    4560 cgctcatgag acaataaccc tgataaatgc ttcaataata ttgaaaaagg a agagtatga    4620 gtattcaaca tttccgtgtc gcccttattc cctttttgc ggcatttgc c ttcctgttt    4680 ttgctcaccc agaaacgctg gtgaaagtaa aagatgctga agatcagttg g gtgcacgag    4740 tgggttacat cgaactggat ctcaacagcg gtaagatcct tgagagtttt c gccccgaag    4800 aacgttttcc aatgatgagc acttttaaag ttctgctatg tggcgcggta t tatcccgta    4860 ttgacgccgg gcaagagcaa ctcggtcgcc gcatacacta ttctcagaat g acttggttg    4920 agtactcacc agtcacagaa aagcatctta cggatggcat gacagtaaga g aattatgca    4980 gtgctgccat aaccatgagt gataacactg cggccaactt acttctgaca a cgatcggag    5040
```

```
gaccgaagga gctaaccgct tttttgcaca acatgggggaa tcatgtaact c gccttgatc    5100 gttgggaacc ggagctgaat gaagccatac caaacgacga gcgtgacacc a cgatgcctg    5160 tagcaatggc aacaacgttg cgcaaactat taactggcga actacttact c tagcttccc    5220 ggcaacaatt aatagactgg atggaggcgg ataaagttgc aggaccactt c tgcgctcgg    5280 cccttccggc tggctggttt attgctgata aatctggagc cggtgagcgt g ggtctcgcg    5340 gtatcattgc agcactgggg ccagatggta agccctcccg tatcgtagtt a tctacacga    5400 cggggagtca ggcaactatg gatgaacgaa atagacagat cgctgagata g gtgcctcac    5460 tgattaagca ttggtaactg tcagaccaag tttactcata tatactttag a ttgatttaa    5520 aacttcattt ttaatttaaa aggatctagg tgaagatcct ttttgataat c tcatgacca    5580 aaatccctta acgtgagttt tcgttccact gagcgtcaga ccccgtagaa a agatcaaag    5640 gatcttcttg agatcctttt tttctgcgcg taatctgctg cttgcaaaca a aaaaccac    5700 cgctaccagc ggtggtttgt ttgccggatc aagagctacc aactcttttt c cgaaggtaa    5760 ctggcttcag cagagcgcag ataccaaata ctgtccttct agtgtagccg t agttaggcc    5820 accacttcaa gaactctgta gcaccgccta catacctcgc tctgctaatc c tgttaccag    5880 tggctgctgc cagtggcgat aagtcgtgtc ttaccgggtt ggactcaaga c gatagttac    5940 cggataaggc gcagcggtcg ggctgaacgg ggggttcgtg cacacagccc a gcttggagc    6000 gaacgaccta caccgaactg agatacctac agcgtgagct atgagaaagc g ccacgcttc    6060 ccgaagggag aaaggcggac aggtatccgg taagcggcag ggtcggaaca g gagagcgca    6120 cgagggagct tccaggggga aacgcctggt atctttatag tcctgtcggg t ttcgccacc    6180 tctgacttga gcgtcgattt ttgtgatgct cgtcaggggg gcggagccta t ggaaaaacg    6240 ccagcaacgc ggccttttta cggttcctgg ccttttgctg gccttttgct c acatgttct    6300 ttcctgcgtt atcccctgat tctgtggata accgtattac cgcctttgag t gagctgata    6360 ccgctcgccg cagccgaacg accgagcgca gcgagtcagt gagcgaggaa g cggaagagc    6420 gcccaatacg caaaccgcct ctccccgcgc gttggccgat tcattaatgc a gctggcacg    6480 acaggtttcc cgactggaaa gcgggcagtg agcgcaacgc aattaatgtg a gttagctca    6540 ctcattaggc accccaggct ttacacttta tgcttccggc tcgtatgttg t gtggaattg    6600 tgagcggata acaatttcac acaggaaaca gctatgacca tgattacgcc a agctcggaa    6660 ttaaccctca ctaaagggaa caaaagctgg agct                                 6694
```